United States Patent
Atkinson

(10) Patent No.: US 9,759,706 B2
(45) Date of Patent: Sep. 12, 2017

(54) METHOD AND KIT FOR MONITORING CATALYST FINES IN HEAVY FUEL OIL

(71) Applicant: Parker Hannifin Manufacturing Limited, Hemel Hempstead, Herts (GB)

(72) Inventor: David Atkinson, Chichester (GB)

(73) Assignee: Parker Hannifin Manufacturing Limited, Hemel Hempstead, Herts (GB)

( * ) Notice: Subject to any disclaimer, the term of this patent is extended or adjusted under 35 U.S.C. 154(b) by 0 days.

(21) Appl. No.: 15/064,762

(22) Filed: Mar. 9, 2016

(65) Prior Publication Data

US 2017/0067870 A1   Mar. 9, 2017

(30) Foreign Application Priority Data

Sep. 8, 2015 (GB) .................................. 1515921.3

(51) Int. Cl.
*G01N 33/28* (2006.01)
*C10G 19/02* (2006.01)
(Continued)

(52) U.S. Cl.
CPC .......... *G01N 33/2858* (2013.01); *C09K 3/00* (2013.01); *C10G 19/02* (2013.01); *C10G 21/02* (2013.01);
(Continued)

(58) Field of Classification Search
CPC ..................................................... G01N 33/28
(Continued)

(56) References Cited

U.S. PATENT DOCUMENTS

| | | | | |
|---|---|---|---|---|
| 1,423,049 A | * | 7/1922 | Tunison ..................... | C10L 1/18 44/401 |
| 1,907,309 A | * | 5/1933 | Schaack, Jr. ............ | C10L 1/023 44/438 |

(Continued)

FOREIGN PATENT DOCUMENTS

| | | |
|---|---|---|
| EP | 3 121 596 A1 | 1/2017 |
| GB | 2 069 693 A | 8/1981 |

(Continued)

OTHER PUBLICATIONS

Holmquist, G. S. et al, Industrial Management 1920, 59, 114-117.*
(Continued)

*Primary Examiner* — Arlen Soderquist
(74) *Attorney, Agent, or Firm* — Christopher Hunter

(57) ABSTRACT

A kit and method for monitoring for the presence of catalyst fines in heavy fuel oil (HFO), including: a) providing a sample of HFO; b) mixing the HFO sample with a diluent composition comprising a non-polar solvent and with an aqueous reagent composition to provide a test sample, wherein the aqueous reagent composition comprises at least one water soluble inorganic salt and at least one water soluble base; c) allowing phase separation to occur in the test sample to provide an aqueous phase and an organic phase; and d) inspecting the aqueous phase of the test sample for the presence of catalyst fines. The diluent composition can consist of a non-polar solvent selected from mineral spirits, kerosene, naphtha, and heavy distillate and a phase transfer agent selected from tripropylene glycol monomethyl ether, ethylene glycol, propyl alcohol, isopropyl alcohol and butanol.

18 Claims, 2 Drawing Sheets

(51) Int. Cl.
- *C10G 21/02* (2006.01)
- *C10G 21/06* (2006.01)
- *C09K 3/00* (2006.01)
- *G01N 31/02* (2006.01)

(52) U.S. Cl.
CPC .......... *C10G 21/06* (2013.01); *G01N 31/02* (2013.01); *G01N 33/2835* (2013.01)

(58) Field of Classification Search
USPC .......... 422/72, 430; 436/37, 40, 60, 164, 177
See application file for complete search history.

(56) References Cited

U.S. PATENT DOCUMENTS

| | | | | |
|---|---|---|---|---|
| 2,445,064 A * | 7/1948 | Hall | C11D 13/02 | 252/192 |
| 2,582,254 A * | 1/1952 | Hunter | B01J 21/12 | 208/52 CT |
| 2,670,362 A * | 2/1954 | Ziegler | C11B 3/001 | 554/192 |
| 3,085,101 A * | 4/1963 | Eger | C11B 3/06 | 554/197 |
| 3,623,983 A * | 11/1971 | Pattenden | C10M 1/08 | 252/389.2 |
| 3,819,508 A * | 6/1974 | Fainman | C10M 175/0016 | 208/180 |
| 3,849,318 A * | 11/1974 | Miner | C10M 1/08 | 508/154 |
| 4,001,109 A * | 1/1977 | Li | B01D 61/40 | 210/638 |
| 4,018,804 A * | 4/1977 | Schneider | C07D 307/33 | 549/268 |
| 4,106,907 A * | 8/1978 | Charlton | G01T 7/02 | 422/405 |
| 4,155,909 A * | 5/1979 | Sanders | A01N 43/40 | 544/124 |
| 4,167,397 A * | 9/1979 | Grant | C10L 9/02 | 201/17 |
| 4,203,725 A | 5/1980 | Snowden | | |
| 4,238,197 A | 12/1980 | Eisentraut | | |
| 4,272,360 A * | 6/1981 | Bialek | C10G 33/04 | 166/267 |
| 4,279,752 A * | 7/1981 | Sueoka | B01D 67/003 | 210/500.22 |
| 4,333,908 A * | 6/1982 | Maki | G01N 33/2835 | 422/430 |
| 4,334,065 A * | 6/1982 | Chauvette | C07D 501/18 | 540/230 |
| 4,444,775 A * | 4/1984 | Ford | C07C 43/32 | 514/300 |
| 4,474,885 A | 10/1984 | Maki | | |
| 4,572,297 A * | 2/1986 | Thigpen, Jr. | C09K 8/607 | 166/307 |
| 4,786,326 A * | 11/1988 | Grove | B27K 3/16 | 106/15.05 |
| 4,841,045 A * | 6/1989 | Kuehne | C07D 487/04 | 540/478 |
| 4,846,847 A * | 7/1989 | Nelson, Jr. | C10L 1/18 | 44/309 |
| 4,889,618 A * | 12/1989 | Tyson, Jr. | C10G 19/02 | 208/113 |
| 4,946,597 A * | 8/1990 | Sury | B03B 9/02 | 208/332 |
| 5,057,152 A * | 10/1991 | Marcus | C09G 1/02 | 106/11 |
| 5,087,268 A * | 2/1992 | Parish | C07C 205/24 | 44/312 |
| 5,145,523 A * | 9/1992 | Halpin | C11D 7/24 | 106/285 |
| 5,316,664 A * | 5/1994 | Gregoli | B01F 3/0811 | 208/390 |
| 5,426,206 A * | 6/1995 | Jung | C07D 303/14 | 556/436 |
| 5,449,686 A * | 9/1995 | Christensen, IV | C07C 45/44 | 514/330 |
| 5,457,208 A * | 10/1995 | Portoghese | C07D 489/06 | 546/35 |
| 5,476,988 A * | 12/1995 | Hart | B01D 21/01 | 208/180 |
| 5,481,059 A * | 1/1996 | Brock | C10G 31/00 | 208/177 |
| 5,593,572 A * | 1/1997 | Hart | C10G 31/00 | 208/177 |
| 5,639,513 A * | 6/1997 | Latham | B05D 1/20 | 118/402 |
| 5,646,207 A * | 7/1997 | Schell | C03C 25/26 | 524/104 |
| 5,681,451 A * | 10/1997 | Hart | C10G 31/00 | 208/177 |
| 5,728,657 A * | 3/1998 | Campbell | C10M 159/22 | 508/460 |
| 5,746,909 A * | 5/1998 | Calta | C10G 1/047 | 208/390 |
| 6,160,141 A * | 12/2000 | Seidel | A61K 31/231 | 554/126 |
| 6,221,823 B1 * | 4/2001 | Crisanti | C11D 3/0084 | 510/238 |
| 6,306,363 B1 * | 10/2001 | Funakoshi | C01B 39/22 | 423/710 |
| 6,462,011 B1 * | 10/2002 | Collins | C11D 1/62 | 510/188 |
| 6,491,824 B1 * | 12/2002 | Lin | B01D 17/00 | 210/666 |
| 6,583,097 B2 * | 6/2003 | McDonald | C11D 1/72 | 510/245 |
| 7,244,364 B1 | 7/2007 | Weber | | |
| 7,286,633 B1 * | 10/2007 | Hardman | G01N 23/223 | 378/45 |
| 2001/0018453 A1 * | 8/2001 | Seidel | A61K 31/201 | 514/547 |
| 2001/0049451 A1 * | 12/2001 | Seidel | C07C 51/377 | 554/127 |
| 2002/0132230 A1 * | 9/2002 | Anderson | B01L 3/5021 | 435/5 |
| 2005/0209123 A1 * | 9/2005 | Laux | C11D 7/5004 | 510/407 |
| 2009/0120836 A1 * | 5/2009 | Weber | C10G 31/08 | 208/13 |
| 2009/0142228 A1 * | 6/2009 | Addicks | B01L 9/54 | 422/400 |
| 2010/0249485 A1 * | 9/2010 | Mdleleni | C10G 2/30 | 585/858 |
| 2012/0301970 A1 * | 11/2012 | Lynn | G01N 31/16 | 436/129 |
| 2014/0333304 A1 * | 11/2014 | Jensen | G01N 24/085 | 324/309 |
| 2015/0160179 A1 * | 6/2015 | Atkinson | G01N 31/22 | 436/60 |
| 2015/0191660 A1 * | 7/2015 | Englund | C10G 31/10 | 585/865 |
| 2016/0122661 A1 * | 5/2016 | Mackel | C10G 33/06 | 208/177 |
| 2016/0326130 A1 * | 11/2016 | Changoer | C07D 311/80 | |

FOREIGN PATENT DOCUMENTS

| | | |
|---|---|---|
| JP | 2005030815 A | 2/2005 |
| JP | 2013019763 A | 1/2013 |

OTHER PUBLICATIONS

Gerin, F. L., Journal of the American Society for Naval Engineers 1948, 60, 691-701.*
Schrakamp, J. W. A. et al, Fuels and New Propellants 1964, 63-88.*
Aldrich Chemical Company Catalog 1988, pp. 1075, 2062, 2128-20129, 2163-2167 and 2187.*

(56) References Cited

OTHER PUBLICATIONS

ASTM D 2273-05 Standard Method for Trace Sediment in Lubricating Oils 2005, 3 pages.*
Procedure: Centrifuge Test for Oil BS&W Cut 2010, 3 pages, downloaded from http://haltechtesting.com/staff/safety/Procedures/pdf/PROCEDURE%20-%20Centrifuge%20Test%20for%20Oil%20BS&W%20Cut.pdf.*
Material Safety Data Sheet for Goo Gone. 2010, 4 pages.*
Parker Kittiwake Cold Corrosion Test Kit Announcement Feb. 2014, 2 pages, downloaded from http://www.kittiwake.com/news/2014/02/Ki.*
Kittiwake Reagent D Safety Data Sheet Mar. 2014, 7 pages, downloaded from http://kittiwake.com/sites/default/files/pdf/Kittiwake-Reagent-D-AS-K10104-KW.pdf.*
Chemical Book information regarding Heavy Distillate CAS#: 64741-65-7, 2016, 1 page, downloaded from http://www.chemicalbook.com/productchemicalpropertiescb9248180_en.htm.*
Hanzevack, E. L. et al, Oil & Gas Journal (Jul. 1980), 78, 74-78.*
Williams, J., Oil & Gas Journal (Nov. 1990), 88, 74-78.*
Leffler, W. L., "Petroleum Refining in Non-Technical Language", PennWell Corporation, 3rd ed., Tulsa, Oklahoma, 2000. Last 3 paragraph on p. 24 and figure 3.2 on p. 25.
Det Norske Veritas AS (DNV), "Engine Worn Out in Less than 100 hours by Catalytic Fines", https://exchange.dnv.com/CasualtyInformation/Documents/Download/53, Dec. 2010, accessed Jan. 28, 2016.
Thornton, R. H. et al., "Marine Fuels and International Standards", Marine Fuels, ed. C. H. Jones, ASTM Special Technical Publication 878, Philadelphia, PA, 1983, ch. 1, p. 10.
"Notes on Heavy Fuel Oil", American Bureau of Shipping, Houston, TX, 1984.
Han, In-Su et al., "Modeling and Optimization of a Fluidized Catalytic Cracking Process under Full and Partial Combustion Modes", Chemical Engineering and Processing, Aug. 2004, 43, 1063-1084.
Tveit, Olav, "Marpol Annex VI—Solving the Low Sulphur Issue", 184, Gard News, Arendal, Norway, Nov. 1, 2006.
Kokarakis, J et al., "Challenges Associated with the Use of Low Sulphur Fuels", SNAME Technical Paper, Jul. 3, 2013. Paper summary only.
Halle, D. O. et al., "High Catalyst Fines Levels Found in Low Sulphur Fuel", Lloyd's List, London, Mar. 20, 2008.
Sherzer, Julius, "Octane-Enhancing Zeolite FCC Catalysts: Scientific and Technical Aspects", Marcel Dekker Inc., New York, 1990. pp. 21-22 only.
Buchanan, J. S. et al., "Mechanistic Considerations in Acid-Catalyzed Cracking of Olefins", J. Catalysis, Jan. 1996, 158(1), (Abstract). Abstract only.
Boerefijn, R. et al., "A Review of Attrition of Fluid Cracking Catalyst Particles", Adv. Powder Technol., 2000, 11(2), (Abstract). Partial Abstract only.
Htay, Mu Mu et al., "Preperation of Zeolite Y Catalyst for Petroleum Cracking", Proceedings of the World Academy of Science: Engineering and Technology, 2008, 48, 114-120.
Hattori, H. et al., "Solid Acid Catalysis From Fundementals to Applications", CRC Press, Boca Raton, FL, 2015, p. 156.
Ford, Mark C., "A Master's Guide to: Using Fuel Oil Onboard Ships", Charles Taylor & Co. Ltd., London, Feb. 2012.
ISO 8217:2012, Specifications of Marine Fuels, Table 2, International Organization for Standardization, Geneva, 2012.
Bejger Artur et al., "Analysis of Tribiological Processes Occuring in Precision Pairs Based on Example of Fuel Injection Pumps of Marine Diesel Engines", Zesz. Nauk. Akad. Morsk. Szczecinie, 2015, 41 (113), 9-16.
Rolsted, Henrik et al., "Onboard Fuel Oil Cleaning, the Ever Neglected Process How to Restrain Increasing Cat-Fine Damages in Two-Stroke Marine Engines", CIMAC Congress Proceedings, Conseil International des Machines A Combustion, Shanghai, 2013.
Boutsikas, Angelos, "The Bunkering Industry and Its Effect on Shipping Tanker Operations", MSc Dissertation, Massachusetts Institute of Technology, 2004.
McMahon, Liz, "Operators to be Told to Take Responsibility for Cat Fines Damage", Lloyd's List, London, Sep. 20, 2013.
ASTM D5184-91, "Standard Test Methods for Determination of Aluminum and Silicon in Fuel Oils by Ashing, Fusion, Inductively Coupled Plasma Atomic Emission Spectrometry, and Atomic Absorption Spectrometry", ASTM International, West Conshohocken, PA, 2012, www.astm.org.
IP501/05, "Determination of Aluminium, Silicon, Vanadium, Nickel, Iron, Sodium, Calcium, Zinc and Phosphorous in Residual Fuel Oil by Ashing, Fusion and Inductively Coupled Plasma Emission Spectrometry", Energy Institute, London, 2005.
ISO 10478:1994, "Determination of Aluminium and Silicon in Fuel Oils—Inductively Coupled Plasma Emission and Atomic Absorption Spectroscopy Methods", Geneva, 2012. First page only.
Noria Corporation, "Elemental Analysis", Practicing Oil Analysis Magazine, Jan. 2002.
Moioli, P. et al;, "Analysis of Art Oobjects Using a Portable X-Ray Fluorescence Spectrometer", X-Ray Spectrom., 2000, 29, 48 (Abstract). Abstract only.
Thermo Fisher Scientific, "Easy Elemental Analysis of Heavy Fuel Oils Using Wavelength Dispersive X-ray Fluorescence", Analytical Instrumentation, Jun./Jul. 26-27,2010.
Maersk Fluid Technology, "Advantages of Using the SEA-Mate Elemental Analyzer", http://www.maersk fluid.com/Index.php/advantages-analyzer, 2016, accessed Jan. 29, 2016.
Sorenson, Morten K. et al., "NMR Sensor for Onboard Ship Detection of Catalytic Fines in Marine Fuel Oils", Anal. Chem., Jul. 2, 2014, 86, 7205 (Abstract). Abstract only.
Schramm, J. et al., "Modelling of Corrosion of Cylinder Liner in Diesel Engines Caused by Sulphur in the Diesel Fuel," SAE Technical Paper 940818, Mar. 1, 1994, doi:10.4271/940818 (Abstract). Abstract only.
Coant, P:. M. et al., "Development of Antiwear Cylinder Oil for High Output Crosshead Diesels", CIMAC Congress Proceedings, Conseil International des Machines A Combustion, Tokyo, 1977 (Abstract). Abstract only.
Parker Kittiwake, "LinerSCAN—A New Era in Asset Protection", http://www.kittiwake.com/sites/default/files/MAK27243 KW&20LinerSCAN%20Brochure%20Single%20Pages.pdf, 2016, accessed Jan. 29, 2016.
GB Patent Application GB1515921.3 entitled "Method", filed on Sep. 8, 2015.
Greensfelder, B. S. et al., "Catalytic and Thermal Cracking of Pure Hydrocarbons", Ind. Eng. Chem., Nov. 1949, 41, 2573-2584.
Roussel, Jean-Claude et al., "Composition of Crude Oils and Petroleum Products", in Crude Oil Petroleum Products Process Flowsheets, ed. J. -P. Wauquier, Editions Technip, Paris, 1994, ch.1, p. 1. First page only.
Pereira, Juan et al., "Breaking of Water-in-Crude oil Emulsions. 4. Estimation of the Emulsifier Surfactant Performance to Destabilize the Asphaltenes Effect", Energy & Fuels, 2011, 25, 1045-1050.
C. M. Technologies, "Innovation Helps to Avoid Wear in Ship Engines", Shipbuilding Industry, 2015, 9(6), 36-37.
ASTM D1796-11e1, "Standard Test Method for Water and Sediment in Fuel Oils by the Centrifuge Method (Laboratory Procedure)", ASTM International, West Conshohocken, PA, 2011, www.astm.org, 623-626.
Stanhope Seta, "Seta Oil Test Centrifuge", http://www.stanhopeseta.co.uk/product.asp?ID=4807&bShowDetail=true, accessed Feb. 1, 2016.
Zendehdel, M. et al., "Efficiency Evaluation of NaY Zeolite and TiO2/NaY Zeolite in Removal of Methylene Blue Dye From Aqueous Solutions", J. Environ. Health. Sci. Eng., 2011, 8(3), 265-272.
Gecgel, Unal et al., Removal of Methylene Blue from Aqueous Solution by Activated Carbon Prepared from Pea Shells (Pisum sativum), Journal of Chemistry, 2013, DOI:10.1155/2013/614083.
Cook, Albert et al., "The Blue Bottle Experiment Revisited", J. Chem. Ed., Feb. 1994, 71.2, 160. First page of a full text preview of the document.

(56) References Cited

OTHER PUBLICATIONS

Singhal, G. S. et al., "Changes in the Absorbtion Spectrum of Methylene Blue with pH", J. Phys. Chem., 1967, 71 (10), 3347. First page only.
Search Report for British Patent Application GB1515921.3 dated Jun. 20, 2016.
Combined Search and Examination Report for GB1615238.1 dated Jul. 3, 2017.
Parker Kittiwake, Safety Data Sheet Kittiwake Reagent D, kittiwake.com, [online], available from: http://kittiwake.com/sites/default/files/pdf/Kittiwake-Reagent-D-ASK10104-KW.pdf, Dec. 3, 2015.
Evian, "Uniquely balance, unlike any other", http://www.evian.com/en_gb/evian_and_your_health/renew_yourself_naturally/uniquely_balanced%20unlike_any_other/; accessed by UK Examiner Jun. 30, 2017.

\* cited by examiner

METHOD AND KIT FOR MONITORING CATALYST FINES IN HEAVY FUEL OIL

FIELD OF THE INVENTION

The invention relates to methods for monitoring for the presence of catalyst fines in a hydrocarbon composition, as well as to reagents and kits for use in such methods. The invention particularly relates to methods of monitoring for the presence of catalyst fines in oil such as heavy fuel oil (HFO) for marine engines.

BACKGROUND

Long chain hydrocarbons present in crude oil are catalytically cracked to increase the yield of valuable short chain hydrocarbons. Unfortunately, the cracking catalysts cannot be completely recovered during the refinery process. As a result, fuels obtained from refinery processes may contain residual catalyst particles (known as catalyst fines or cat fines).

Catalyst fines are predominantly found in fuel oils, and in particular in number 6 fuel oils or heavy fuel oils. Fuel oils are essentially the residue left behind after the useful short chain hydrocarbons have been removed. Fuel oils are therefore the heaviest commercial fuel that can be obtained from crude oil, i.e., heavier than gasoline and naphtha.

It is generally accepted that there are 6 different classes of fuel oil; these are detailed below. The boiling point and carbon chain length of the fuel increases with fuel oil number. Viscosity also increases with number, and the heaviest oil has to be heated to get it to flow.

Number 1 fuel oil is a volatile distillate oil intended for vaporizing pot-type burners. The carbon chain length is typically between 9-16 carbon atoms. Number 2 fuel oil is used either as a home heating oil or as fuel for automobiles, trucks, lorries etc. The carbon chain length is typically between 10-20 carbon atoms. Number 3 fuel oil is a distillate oil for burners requiring low-viscosity fuel. Number 3 fuel oil is now commonly blended with number 2 fuel oil. Number 4 fuel oil is a commercial heating oil for burner installations not equipped with preheaters. The carbon chain length is typically between 12-70 carbon atoms. Number 5 fuel oil is a residual-type industrial heating oil requiring preheating for proper atomization. The carbon chain length is typically between 12-70 carbon atoms.

Number 6 fuel oil is a high-viscosity residual oil requiring preheating to 104-127° C. for ignition. In this context, residual refers to the material remaining after the more valuable fractions of crude oil have been evaporated. The residue usually contains various undesirable impurities, including water, sulphur and catalyst fines. Number 6 fuel oil is also known as residual fuel oil (RFO), heavy fuel oil (HFO), by the Navy specification of Bunker C, or by the Pacific Specification of PS-400. The carbon chain length is typically between 20-70 carbon atoms.

As used herein, the term heavy fuel oil or HFO is referring to number 6 fuel oil or any equivalent thereof. Because of the impurities present in HFO, it is very cheap. In fact, it is the cheapest liquid fuel available. Since it requires heating before use, residual fuel oil cannot be used in road vehicles, as the heating equipment takes up valuable space and makes the vehicle heavier. Heating the HFO is also a delicate procedure, which is inappropriate to do on small, fast moving vehicles. However, marine vessels are typically capable of accommodating the heating equipment necessary to use HFO as a fuel source.

Marine vessels are equipped with settling tanks and purifiers that should reduce the concentration of catalyst fines in the fuel pumped aboard, which according to ISO 8217:2012 should be less than 60 ppm, to beneath the limit recommended by engine manufacturers (15 ppm). Very significant damage can occur to engines if they encounter higher concentrations of cat fines due to, for example, the use of fuel that is not ISO compliant, problems with the fuel purifiers, or rough weather kicking up fines from the bottom of the settling tanks.

Use of HFO as a fuel source is not limited to marine vessels, and historically HFO has been used to power other large engines, such as those found in boilers on steam locomotives, and in large or industrial buildings. HFO is also used to start up boilers in many coal fired power plants.

While there are obvious environmental concerns owing to the presence of residual sulphur in HFO, the presence of catalyst fines is particularly problematic, as catalysts fines are very hard particles that can cause significant damage to engines. In particular, in marine vessels, catalyst fines can cause damage to the cylinder liners. Monitoring for the presence of catalyst fines in HFO is therefore desirable, as it can act as an indicator of the likelihood of damage by catalyst fines from a particular batch of HFO.

Existing methods for detecting catalyst fines are either inadequate, expensive or time consuming. For example, sophisticated equipment has been developed that uses spectroscopy to determine the amount of catalyst fines passing into the engines of the vessel. Examples are the NanoNord Catguard and the Maersk Fluid Technology Sea-Mate M3000 Analyser, which use NMR and XRF spectrometry respectively. However, the high cost (c.a. £50,000) of these machines limits their usefulness. Moreover, such high accuracy methods are overcomplicated; in general, the person in charge of the engine simply needs to know whether there is a significant level of catalyst fines present or not.

It is therefore desirable to find a simple, low cost way to monitor for the presence of catalyst fines in a hydrocarbon sample, particularly heavy fuel oil (HFO).

SUMMARY OF THE INVENTION

In a first embodiment, the present invention is directed towards a method for monitoring for the presence of catalyst fines in heavy fuel oil (HFO), said method comprising:
a) providing a sample of HFO;
b) mixing the HFO sample with a diluent composition comprising a non-polar solvent and with an aqueous reagent composition to provide a test sample, wherein the aqueous reagent composition comprises at least one water soluble inorganic salt and at least one water soluble base;
c) allowing phase separation to occur in the test sample to provide an aqueous phase and an organic phase; and
d) inspecting the aqueous phase of the test sample for the presence of catalyst fines.

In a second embodiment, the present invention is directed towards a diluent composition consisting of a non-polar solvent selected from mineral spirits, kerosene, naphtha, and heavy distillate (CAS #64741-65-7) and a phase transfer agent selected from tripropylene glycol monomethyl ether, ethylene glycol, propyl alcohol, isopropyl alcohol and butanol.

In a third embodiment, the present invention is directed towards kits for use in the present invention and to the use of said kits to detect the presence of catalyst fines in heavy fuel oil (HFO).

FIGURES

DETAILED DESCRIPTION OF THE INVENTION

Figure 1:
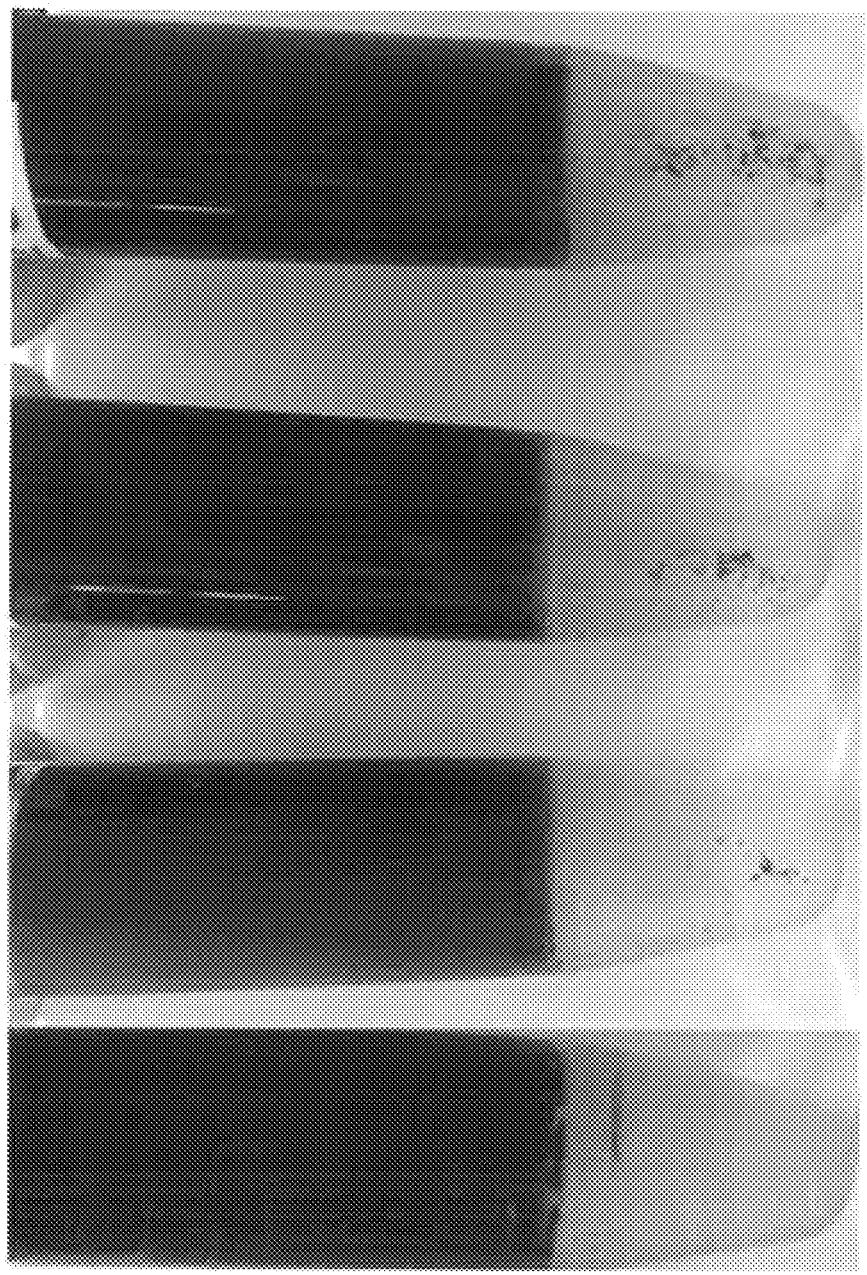
FIG. 1 is a photograph showing the results of applying the test method of the invention to HFO samples that contain 0 ppm, 50 ppm, 100 ppm, and 200 ppm of catalyst fines respectively.

The present invention provides a method for monitoring for the presence of catalyst fines in a sample of heavy fuel oil (HFO), and reagents and kits for use in the same. By establishing the presence or absence of catalyst fines, and optionally also determining the rough amount of catalyst fines present in the HFO sample, action can be taken to mitigate damage which may be caused by these fines.

The terms "catalyst fines" and "cat fines" are used interchangeably herein. Catalyst fines, as indicated above, are particles of catalyst (typically 1-75 μm in diameter) that are left behind after cracking of crude oil. Zeolites are microporous, aluminosilicate minerals commonly used as commercial adsorbents and catalysts. In particular, zeolites make excellent cracking catalysts because they have a well-defined porous structure with a large surface area that can be readily chemically modified. Thus, catalyst fines are usually zeolite particles.

The concentration of catalyst fines as used herein (and as generally quoted in the art) is the combined mass of aluminium plus silicon within a sample. According to ISO 8217:2012 for marine fuels, the combined mass of aluminium plus silicon in the fuel should be less than 60 ppm. However, engine manufacturers recommend that the presence of Al+Si does not exceed 15 ppm. It is important to note that when catalyst fine concentrations are quoted herein or in the art, they are actually referring to the sum of the aluminium and silicon contained within sample; the actual particle concentration [in ppm] will be much higher, as zeolites contain atoms other than Al and Si. For example, a combined Al+Si mass concentration of 60 ppm roughly corresponds to a particle concentration of 200 ppm (i.e. 200 mg of catalyst fine particles per kilo of HFO).

The various compositions and steps which are involved in the method of the invention will now be described in more detail.

By "refinery process" is meant a process in which hydrocarbons are separated using fractional distillation and/or converted using heat in processes such as thermal cracking.

As noted above, the method of the invention finds particular use for detecting catalyst fines in heavy fuel oil (HFO) for use in combustion engines, particularly combustion engines on marine vessels.

By "marine vessels" is meant ships and boats. A "marine engine" is therefore a combustion engine on a ship or boat.

In theory, a diluent composition may not be needed if it is possible to mix the sample of HFO with the aqueous reagent composition to allow separation of the catalyst fines. However, this can lead to inaccuracies as HFO is particularly viscous. Due to the high viscosity of heavy fuel oil, it is physically incapable of mixing with the aqueous reagent composition in a reasonable timescale and without significant input of energy (such as by agitation, heating or sonication).

Thus, while the method of the invention could, in theory, be carried out without a diluent composition being present, some other step would then be necessary to get the aqueous reagent composition to mix sufficiently with the HFO. This increases both the complexity and cost of the method, and is therefore disfavoured. Instead, a relatively small amount of HFO may be used in combination with a diluent composition, such that the test sample contains majority of aqueous reagent composition and diluent composition.

The diluent composition comprises at least one non-polar solvent, which reduces the viscosity of the heavy fuel oil rendering it capable of being mixed with the aqueous reagent composition and allowing subsequent separation of the test sample into two phases, an aqueous phase and an organic (non-aqueous) phase.

The diluent composition may be combined with the heavy fuel oil prior to mixing with the reagent composition to form the test sample. Alternatively, the diluent composition can be added to the aqueous reagent composition prior to addition of the heavy fuel oil. Alternatively, the diluent composition, reagent composition and heavy fuel oil can be combined simultaneously to form the test sample.

By "non-polar solvent" is meant a solvent with a low dielectric constant, preferably with a dielectric constant below 5. As used herein, the dielectric constant is measured at 25° C., for example using a BI-870 from Brookhaven Instruments.

Suitable non-polar solvents include aliphatic hydrocarbons, aromatic hydrocarbons and ethers, with aliphatic hydrocarbons, aromatic hydrocarbons and mixtures thereof being preferred.

The non-polar solvent preferably has relatively low volatility, flammability and viscosity. Therefore, highly volatile aliphatic hydrocarbons such as pentane and low boiling petroleum ethers are less preferred. Thus, while such solvents generally work perfectly well, on a practical level they are less favourable to work with due to safety concerns which inevitably arise when using volatile and flammable solvents.

Preferred non-polar solvents include petroleum distillates, such as mineral spirits, kerosene, naphtha, and heavy distillate (CAS #64741-65-7), with naphtha and heavy distillate being particularly preferred. It is also preferred that the non-polar solvent does not consist solely of or comprise toluene.

When carrying out the method of the invention, sufficient diluent composition should be used to dilute the heavy fuel oil (i.e. reduce its viscosity) enough to allow mixing with the reagent composition, and thereby allow the cat fines to move out of the organic phase and into the aqueous phase.

Sufficient diluent composition should be used such that the organic phase will float above the aqueous phase. In general, heavy fuel oil has a density slightly lower than 1 g/cm$^3$, and will therefore float on water. However, some samples of HFO can have a density slightly higher than that of water. In such cases, sufficient diluent composition should be added such that the organic phase will float above the aqueous phase.

However, excessive amounts of diluent composition will make the method more cumbersome and increase costs, both in terms of needing to purchase more diluent composition, and the costs associated with waste disposal. For this reason, the amount of diluent composition used in the method of the invention is preferably between about 1 ml and about 100 ml, more preferably, between about 2 ml and about 50 ml.

Similarly, to reduce costs the amount of heavy fuel oil (HFO) used in the method of the invention is preferably relatively small. Thus, the method of the invention is generally carried out using a sample size of up to 10 ml of HFO, for example approximately 5 to 6 ml. This sample of HFO may be removed from a batch using any suitable sampling means. For example, particularly if the HFO is slightly warmed, sampling via syringe may be possible.

The regent composition comprises water and is aqueous (i.e. water constitutes at least 50% by volume of all of the liquid in the reagent composition). The reagent composition additionally comprises at least one water soluble inorganic salt and at least one water soluble base. Due to the presence of the at least one water soluble base, the reagent composition has a pH of 7.5 or above.

There is no particular limitation on the type of water that can be used in the regent composition. However, for improved reliability and consistency between tests, use of deionised or distilled water is preferred.

There is no particular limitation on the nature of the at least one inorganic salt. However, it must be soluble in water. The presence of the salt increases the ionic strength of the aqueous reagent composition. The higher the ionic strength of the reagent composition, the greater the tendency for the aqueous phase to separate from the organic phase in the test sample.

It is also preferable that the at least one inorganic salt does not impart any colour to the aqueous phase. This is not because coloured salts will not work but merely for practical reasons, as the presence of highly or dark coloured salts may make the results of the test more difficult to see. For ease of handling and disposal, use of non-toxic salts is also preferred. Thus, preferably the cation of the inorganic salt is not a heavy metal such as cadmium, mercury, lead or arsenic.

The at least one water soluble inorganic salt is preferably a nitrate salt, a sulfate salt other than calcium sulfate, a halide salt other than a silver halide, sodium carbonate or potassium carbonate.

More preferably, the at least one water soluble inorganic salt is a nitrate salt of a non-toxic metal, a sulfate salt of any non-toxic metal other than calcium (calcium sulfate is insoluble in water), a halide salt of a non-toxic metal (but not a silver halide), sodium carbonate or potassium carbonate.

For commercial reasons, use of lower cost salts is generally preferred. Thus, the water soluble inorganic salt is preferably one or more salts selected from the group consisting of magnesium sulphate, ammonium sulphate, sodium carbonate, potassium carbonate, sodium chloride and potassium chloride. Use of sodium chloride as the water soluble inorganic salt is particularly preferred.

There is no particular limitation on the nature of the at least one water soluble base. However, as with the inorganic salt discussed above, for practical reasons the water soluble base preferably does not impart any colour to the aqueous phase and is non-toxic.

Without wishing to be bound by theory, it is thought that the presence of the water soluble base in the aqueous reagent composition helps keep the walls of the lower part of the separating vessel clear. In particular, these walls are kept free from oil smears. Any oil that clings to the walls of the vessel below the water-line is problematic as it can obscure the catalyst fines, making the test results difficult to evaluate.

Preferred bases include oxides and hydroxides of non-toxic metals, as well as carbonates and hydrogen carbonates of non-toxic metals. Preferably the water soluble base is a hydroxide of a Group I or Group II metal. More preferably, the water soluble base is at least one base selected from the group consisting of lithium hydroxide, sodium hydroxide, potassium hydroxide, magnesium hydroxide and calcium hydroxide. Use of sodium hydroxide as the water soluble base is particularly preferred.

A preferred aqueous reagent composition for use in the method of the invention comprises distilled or deionised water, at least one water soluble salt that is selected from the group consisting of magnesium sulphate, ammonium sulphate, sodium carbonate, potassium carbonate, sodium chloride and potassium chloride and at least one water soluble base that is selected from the group consisting of lithium hydroxide, sodium hydroxide, potassium hydroxide, magnesium hydroxide and calcium hydroxide.

A particularly preferred aqueous reagent composition for use in the method of the invention comprises distilled or deionised water, sodium chloride as the water soluble salt and sodium hydroxide as the water soluble base.

When carrying out the method of the invention, sufficient aqueous reagent composition should be used such that the organic and aqueous phases are clearly visible after phase separation in the test sample. However, excessive amounts of aqueous reagent composition will make the method more cumbersome and increase costs. The amount of aqueous reagent composition will normally be roughly equivalent to, or slightly less than, the amount of the organic phase (i.e. the total amount of the diluent composition and heavy fuel oil).

The aqueous reagent composition is formed by dissolving the water soluble inorganic salt and water soluble base in water. The water soluble inorganic salt and water soluble base can be added to the water separately or together. It may be necessary to employ some sort of stirring means to fully dissolve the salt and base in the water. This may involve use of mechanical stirring means, such as an overhead stirrer or magnetic stirrer bar.

As indicated above, the presence of the water soluble inorganic salt increases the ionic strength of the aqueous reagent solution. Thus, it is preferable to have a reasonably high concentration of the water soluble inorganic salt in the aqueous reagent solution, to achieve high ionic strength. However, the aqueous reagent solution should not be saturated, as this can lead to precipitation of salts, which may make the results of the test more difficult to observe.

By way of example, when the salt is sodium chloride and the base is sodium hydroxide, about 240 g of sodium chloride and about 10 g of sodium hydroxide can be dissolved in each liter of water to form an aqueous reagent composition.

Heavy fuel oil is immiscible with the aqueous reagent composition. The test sample therefore phase separates to form an aqueous phase and an organic phase. However, the amount of phase separation can vary. It is therefore preferred to use sufficient diluent composition and aqueous reagent composition in order to ensure that there is clear phase separation in the test sample. The presence of the aqueous reagent phase causes the catalyst fines to partition into the aqueous phase. As the catalyst fines are solid particles, these settle to the bottom of the test sample under gravity. Thus, at the end of the test procedure, three distinct phases may be visible in the test sample, namely, an upper organic (hydrocarbon) phase, a lower aqueous phase and a solid phase containing catalyst fines. Obviously, if no catalyst fines are present, no solid phase will be visible.

An operator can assess whether catalyst fines are present simply by looking at a separated sample produced at the end of the test procedure. As indicated above, FIG. 1 is a photograph showing the results of applying the method of the invention to HFO samples that contain 0 ppm, 50 ppm, 100 ppm, and 200 ppm of catalyst fines respectively. By comparing the results of the test with such a photograph, a skilled person can obtain a rough estimate of the amount of catalyst fines present in a tested HFO sample. However, the aim of the method of the invention is not necessarily to provide a quantitative measurement of the amount of catalyst fines present, but to simply provide a yes/no answer to the question of whether catalyst fines are present.

Although manufacturers state that engines can tolerate up to 15 ppm catalyst fines, it is better if no catalyst fines are present, since then all likelihood of damage by the fines will be removed. If catalyst fines are detected by the test method of the invention this tells the operator that either (a) action is needed to purify the heavy fuel oil e.g. by use of a filtration/purification system, or (b) the heavy fuel oil is of unsuitable quality and an alternative should be sought.

If the skilled person requires a quantitative measure of the amount of catalyst fines present in the aqueous phase, then turbidimetry could be used. Turbidimetry is the process of measuring the loss of intensity of transmitted light due to the scattering effect of particles suspended in it. Light is passed through a filter creating a light of known wavelength which is then passed through a cuvette containing a solution to be tested. A photoelectric cell collects the light which passes through the cuvette. A measurement is then given for the amount of absorbed light. This measurement then correlates to the level of particulates in the test sample. In the present invention, it is envisaged that the aqueous layer could be removed following phase separation, for example using a syringe, and transferred to a cuvette for turbidimetry analysis.

The method of the invention involves mixing the heavy fuel oil with the diluent composition and the reagent composition to form a test sample. By "mixing" is meant that the reagent and diluted heavy fuel oil are combined sufficiently to allow transfer of the catalyst fines from the organic phase to the aqueous phase.

To ensure sufficient mixing of the heavy fuel oil, diluent and aqueous reagent composition, and maximum separation of the catalyst fines, shaking of the test sample is recommended. This may be carried out either manually or mechanically. For example, the test sample may be sealed and manually shaken to mix. Alternatively, mechanical means such as a shaker or a vortex mixer (such as those supplied by Bio Rad e.g. the BR-2000 vortexer) may be used. Equally, stirring apparatus may be used to perform the mixing. Stirring means may be "overhead", such as by use of a paddle system, or "underneath" such as use of a magnetic stirrer pellet. The actual means of mixing is not important, provided that thorough mixing of the heavy fuel oil, diluent composition and aqueous reagent composition occurs.

After mixing, the aqueous and organic phases are allowed to separate. During the mixing step, the catalyst fines move from the organic phase into the aqueous phase. However, due to gravity, the catalyst fines will inevitably settle at the bottom of the aqueous layer. Thus, in one embodiment, the test sample is left after mixing to allow the phases to separate and the catalyst fines to settle under gravity. This typically involves leaving the sample to stand at room temperature in a stable (i.e. undisturbed) place for a period of time. While some settling of the catalyst fines may be visible relatively quickly, it is advisable to leave the sample to settle for at least about an hour before trying to read the results of the test.

It is highly desirable that some or all of the mixed test sample is transferred to a clean container for the separating step to minimise the risk of the test results being obscured. For example, a portion of the mixture can be removed via dropping pipette and transferred to a clean container. Preferably, the clean container is prefilled with a small amount of aqueous reagent composition, and the mixture is added above the additional aqueous composition. Any HFO that comes into contact with the bottom of the separating vessel may adhere to the sides of the vessel, thereby potentially obscuring any cat fines that might otherwise be visible. By adding the mixture to the top of a small amount of aqueous composition, the lower portion of the separating vessel should never come into contact with the HFO, and therefore should remain free from oil smears.

While allowing the test sample to separate under gravity will work, it is relatively slow. The speed of phase separation may be accelerated by use of heat and/or a demulsifying agent. Any demulsifier could be added to the aqueous reagent composition or to the sample before or during mixing. However, these options increase the complexity of the test and the costs involved. For example, if the test sample is to be heated, this should be done in a well-ventilated space, and preferably within a fume hood for safety reasons.

A preferred way to accelerate the phase separation process is to use a centrifuge. Any standard laboratory centrifuge may be used to accelerate the phase separation and settling of the catalyst fines. Examples include Argos Technologies FlexiFuge centrifuge, Thermo Scientific Sorvall™ and SL 8 centrifuges and Beckman Coulter Alegra® and Microfuge® centrifuges.

The samples should be spun in the centrifuge for a time sufficient to effect phase separation. This will depend on the centrifuge speed and sample size. Centrifuges may spin at high speed (up to about 120,000 rpm), thereby exerting considerable force to a sample. In such cases it is expected that some phase separation will be visible after only a few seconds. However, to ensure full phase separation of the sample, centrifugation for a longer period of time is recommended. Thus, centrifugation under high speed is preferably carried out for at least one minute. Centrifuges may spin at lower speed (as low as 2,000 rpm), thereby exerting much less force to a sample. When using a lower speed centrifuge, longer centrifugation times will be necessary. In practice, centrifugation times may vary between about 1 minute and about 30 minutes. A skilled person will be able to readily determine a suitable centrifugation time and speed required to effect phase separation of any particular test sample. By way of illustration, a centrifugation time of about 15 minutes at a centrifuge speed of about 9,000 rpm is typical.

Samples can be removed periodically from a centrifuge and assessed visually for phase separation. Such samples can, if necessary, be returned to the centrifuge for a further time period if phase separation is not visible.

To enhance transfer of the cat fines from the organic phase, a phase transfer agent may be used. A phase transfer agent is miscible or soluble in both the aqueous phase and the organic phase, and is capable of interacting with the catalyst fines to aid in their movement between the two phases.

Preferred phase transfer catalysts are polar solvents such as ethers or alcohols. As with the non-polar solvents discussed above, for practical purposes relatively high-boiling ethers and alcohols are preferred, such as those with boiling points above 50° C. Ethers and alcohols with lower boiling points may function perfectly well. However, there are safety concerns that arise with use of ether and alcohol solvents having low boiling points.

Preferred phase transfer agents include tripropylene glycol monomethyl ether, ethylene glycol, propyl alcohol, isopropyl alcohol and butanol (including n-butanol, sec-butanol and tert-butanol), with tripropylene glycol monomethyl ether being particularly preferred.

The phase transfer agent may be added to any of the compositions prior to the mixing step b) or may be added separately. However, it is preferred that the phase transfer agent forms part of the diluent composition. Thus, preferred diluent compositions comprise both a non-polar solvent and a phase transfer agent.

One preferred diluent composition comprises a non-polar solvent selected from mineral spirits, kerosene, naphtha, and heavy distillate and a phase transfer agent selected from tripropylene glycol monomethyl ether, ethylene glycol, propyl alcohol, isopropyl alcohol and butanol (including n-butanol, sec-butanol and tert-butanol).

Preferred combinations of diluent and phase transfer agents include the following:
  naphtha and tripropylene glycol monomethyl ether;
  heavy distillate and tripropylene glycol monomethyl ether;
  naphtha and isopropyl alcohol;
  heavy distillate and isopropyl alcohol;
  naphtha and ethylene glycol; and
  heavy distillate and ethylene glycol.

Use of heavy distillate and tripropylene glycol monomethyl ether is particularly preferred.

The amount of phase transfer agent should be such that it does not cause precipitation of salt(s) from the aqueous reagent composition.

The method of the invention is carried out in a suitably sized vessel. There is no particular restriction on the size of the vessel. However, to avoid unnecessary wastage of heavy fuel oil, diluent composition and aqueous reagent composition, smaller vessels are preferred, such as those holding up to 50 ml of liquid.

Multiple vessels may be used to carry out a single test, as the separation step may be performed in a different vessel to the mixing step.

To ensure maximum visibility of any catalyst fines present, the walls of the vessel used for the separating step should be transparent, and preferably colourless. Thus, the separating step is preferably carried out in a clear glass or plastic container. If a plastic container is used, care should be taken that the plastic is chemical resistant, and will not soften or deform in the presence of the heavy fuel oil or the diluent.

As indicated above, the separation step may take place in a centrifuge. In such cases, at least the separating step of the method of the invention is carried out in a centrifuge tube. Centrifuge tubes are typically transparent, colourless plastic tubes that can be sealed with lids (either screw top or clip on) prior to placing in the centrifuge. Owing to the clear transparent sides of centrifuge tubes, any phase separation and/or settling of cat fines is clearly visible.

Figure 2:
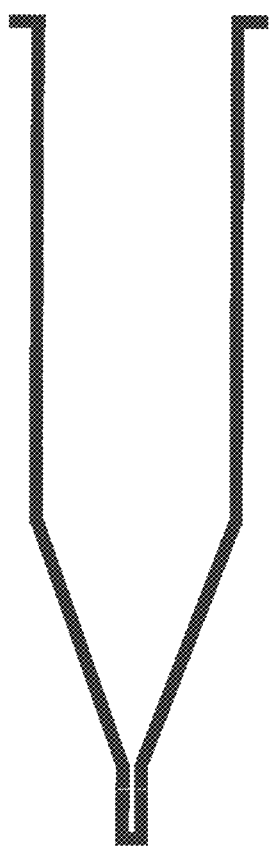
FIG. 2 shows an adapted centrifuge tube which may be used in the method of the invention.

Centrifuge tubes usually have a rounded or conical base in which solids can collect. Thus, one way to establish the amount of catalyst fines present might be to use the depth of precipitate obtained in the base of the centrifuge tube as a rough measurement of the amount of catalyst fines present in a heavy fuel oil. A scale could also be added to the tip of the centrifuge tube to assist in estimating the amount of cat fines present. FIG. 2 shows an adapted centrifuge tube which could be used in such a method.

The present invention further relates to an aqueous reagent composition comprising at least one water soluble inorganic salt and at least one water soluble base, wherein the at least one water soluble inorganic salt is selected from a nitrate salt, a sulfate salt other than calcium sulfate, a halide salt other than a silver halide, sodium carbonate or potassium carbonate; and wherein the and at least one water soluble base is a hydroxide of a Group I or Group II metal.

Preferably, the at least one water soluble inorganic salt is sodium chloride. Preferably, the at least one water soluble base is sodium hydroxide. More preferably, the at least one water soluble inorganic salt is sodium chloride and the at least one water soluble base is sodium hydroxide. Thus, the present invention most preferably further relates to an aqueous reagent composition comprising sodium chloride and sodium hydroxide.

Another embodiment of the invention is directed towards a diluent composition consisting of a non-polar solvent selected from mineral spirits, kerosene, naphtha, and heavy distillate (CAS #64741-65-7) and a phase transfer agent selected from tripropylene glycol monomethyl ether, ethylene glycol, propyl alcohol, isopropyl alcohol and butanol (including n-butanol, sec-butanol and tert-butanol).

Preferably, the non-polar solvent is heavy distillate. Also preferably, the phase transfer agent is tripropylene glycol monomethyl ether. More preferably, the non-polar solvent is heavy distillate and the phase transfer agent is tripropylene glycol monomethyl ether.

The present invention further relates to kits comprising:
a) a diluent composition comprising a non-polar solvent; and
b) an aqueous reagent composition comprising at least one water soluble inorganic salt and at least one water soluble base.

Preferably, the non-polar solvent is heavy distillate.

The diluent composition may further comprises a phase transfer agent, selected from those outlined above. Preferably, in the kits of the invention, the phase transfer agent is tripropylene glycol monomethyl ether.

In the kits of the invention, the aqueous reagent composition is as described above. Thus, preferably, the at least one water soluble inorganic salt is sodium chloride. Preferably, the at least one water soluble base is sodium hydroxide. Most preferably the at least one water soluble inorganic salt is sodium chloride and the at least one water soluble base is sodium hydroxide.

As well as the diluent composition and aqueous reagent composition, the kits of the invention may also comprise equipment to assist with preforming the method of the invention. Obviously, the kits of the invention can be readily tailored to suit individual customer needs. However, the kits may, for example, include one or more items selected from the following list:
  vessels for mixing the heavy fuel oil with the diluent composition and aqueous reagent composition;
  vessels for performing the separation step (if different from the mixing vessel) for example, centrifuge tubes;
  measuring and dispensing equipment such as syringes, dropping pipettes or measuring cylinders for dispensing the heavy fuel oil, diluent composition and aqueous reagent composition;
  a centrifuge for carrying out the separating step; and
  a visual guide for assessing the results of the test (such as FIG. 1).

For ease of carrying out the test, the vessels and/or the measuring/dispensing equipment may be disposable. Either plastic or glass equipment may be used e.g. plastic or glass centrifuge tubes. However, such items are likely to be used in a disposable fashion, as the HFO is difficult to completely remove from surfaces and therefore cleaning the equipment is not generally cost effective.

Preferred kits will contain some or all of the consumables used in the test, including the diluent composition, the reagent composition and/or any disposable vessels or measuring/dispensing equipment. Some of the vessels may be provided pre-filled with suitable amounts of the diluent compositions and/or the aqueous reagent composition for use in the method of the invention.

By way of example, it is envisaged that so-called "starter" kits, suitable for carrying out the method of the invention a certain number (n) of times, would contain the following:
- a centrifuge;
- 2n centrifuge tubes;
- 2n pipettes;
- n syringes;
- a 65 ml bottle containing an aqueous reagent composition;
- n 30 ml bottles pre-filled with an aqueous reagent composition;
- instructions for use in the method of the invention.

'n' may be any number, but it is envisaged that kits will typically enable the consumer to perform the method of the invention at least 10 times, preferably 25 times. Thus, a kit for performing the method of the invention will contain 50 centrifuge tubes and 25×30 ml bottles. Centrifugation must be carried out on a minimum of two samples, to ensure that the machine is balanced, hence 2n tubes.

It is further envisaged that "top-up" kits could be provided, each containing the above but without the centrifuge.

The following non-limiting examples are provided to further illustrate the invention.

The following abbreviations are used herein:
g—gram
HFO—heavy fuel oil
min—minute
ml—milliliter
ppm—parts per million Example 1

Diluent Composition
   1950 g Tripropylene glycol monomethyl ether
   2000 g Heavy distillate
Aqueous Reagent Composition
   2500 g Deionised water
   600 g Sodium chloride
   25 g Sodium hydroxide
Test Procedure
1. 4.1 g of the aqueous reagent composition and 8.7 g of the diluent composition were added to a 30 ml bottle with a lid.
2. A 5 ml syringe was completely filled with HFO by drawing back the plunger until it reached the stop (this means that about 6 ml of HFO was drawn into the syringe). The HFO was warmed slightly to reduce its viscosity enough to allow it to be drawn into the syringe.
3. All of the HFO from the syringe was added to the 30 ml bottle containing the diluent composition and aqueous reagent composition. The lid was secured and the bottle shaken vigorously for 3 min.
4. 4.5 ml of the mixture was removed from the bottle using a dropping pipette.
5. This was added to a 5 ml centrifuge tube containing an additional 0.5 ml of the aqueous reagent composition.
6. Steps 4 and 5 were repeated so that there were two centrifuge tubes, each containing 5 ml of a mixture of HFO, diluent composition and reagent composition.
7. The centrifuge tubes were sealed and placed inside a centrifuge in opposite positions (to balance the machine).
8. The tubes were spun in the centrifuge for 15 min.
9. The tubes were removed and visually inspected.

FIG. 1 shows the results of the above test carried out on samples of HFO known to contain 0 ppm, 50 ppm, 100 ppm and 200 ppm of catalyst fines respectively.

Comparative Example 1

The above test procedure was repeated using toluene as the non-polar solvent in the diluent composition, with no phase transfer catalyst.

Poor separation of the aqueous and organic phases was observed even after centrifugation. Separation of the aqueous and organic phases was eventually achieved by addition of a demulsifying agent and heating the resulting mixture. However, no catalyst fines were visible in the aqueous phase, despite performing this test on a sample of HFO known to contain catalyst fines.

Examples 2 and 3

The test procedure of Example 1 was repeated with alternative aqueous reagent compositions, replacing the sodium chloride with magnesium sulfate (Example 2) or ammonium sulfate (Example 3). These salts can be used at lower concentrations than sodium chloride to provide solutions having similar ionic strength. The salts are therefore less prone to precipitation from solution.

The compositions of these alternative aqueous reagent compositions are shown in Table 1 below:

TABLE 1

| Aqueous reagent compositions | |
|---|---|
| Example 2 | Example 3 |
| 1000 g Deionised water | 1000 g Deionised water |
| 500 g magnesium sulfate (heptahydrate) | 400 g ammonium sulfate |
| 10 g Sodium hydroxide | 10 g Sodium hydroxide |

Separation of the aqueous and organic phases was observed, with the presence of catalyst fines visible in the aqueous phase.

The invention claimed is:

1. A method for monitoring for the presence of catalyst fines in a heavy fuel oil (HFO), said method comprising:
   a) providing a sample of HFO;
   b) mixing the HFO sample with a diluent composition comprising a non-polar solvent and with an aqueous reagent composition to provide a test sample, wherein the aqueous reagent composition comprises at least one water soluble inorganic salt and at least one water soluble base;
   c) allowing phase separation to occur in the test sample to provide an aqueous phase and an organic phase; and
   d) inspecting the aqueous phase of the test sample for the presence of catalyst fines.

2. The method of claim 1, wherein the at least one water soluble inorganic salt is a nitrate salt, a sulfate salt other than calcium sulfate, a halide other than silver halide, sodium carbonate or potassium carbonate.

3. The method of claim 2, wherein the at least one water soluble inorganic salt is sodium chloride.

4. The method of claim 1, wherein the at least one water soluble base is a hydroxide of a Group I or Group II metal.

5. The method of claim 4, wherein the at least one water soluble base is sodium hydroxide.

6. The method of claim 1, wherein the diluent composition comprises a non-polar solvent selected from mineral spirits, kerosene, naphtha, and heavy distillate (CAS #64741-65-7).

7. The method of claim 1, wherein the diluent composition does not comprise toluene.

8. The method of claim 1, wherein the diluent composition further comprises a phase transfer agent.

9. The method of claim 8, wherein the phase transfer agent is selected from tripropylene glycol monomethyl ether, ethylene glycol, propyl alcohol, isopropyl alcohol and butanol.

10. The method of claim 9, wherein the diluent composition comprises heavy distillate and a phase transfer agent that is tripropylene glycol monomethyl ether.

11. The method of claim 1, wherein separation step c) comprises centrifuging the test sample.

12. The method of claim 1, wherein steps b) and c) take place in different containers.

13. The method of claim 1, wherein the diluent composition and the aqueous reagent composition are added to the heavy fuel oil sequentially.

14. The method of claim 1, wherein the diluent composition and the aqueous reagent compositions are added to the heavy fuel oil simultaneously.

15. A kit, comprising: a sealed container containing a diluent composition comprising a non-polar solvent selected from mineral spirits, kerosene, naphtha, and heavy distillate (CAS #64741-65-7); and an aqueous reagent composition comprising at least one water soluble inorganic salt and at least one water soluble base.

16. The kit of claim 15, wherein the diluent composition and aqueous reagent composition are provided in separate sealed containers, are premixed and provided in a single sealed container, or both.

17. The kit of claim 15, wherein the at least one water soluble inorganic salt is sodium chloride.

18. The kit of claim 15, wherein the at least one water soluble base is sodium hydroxide.

* * * * *